(12) United States Patent
Abboud

(10) Patent No.: US 9,925,018 B2
(45) Date of Patent: Mar. 27, 2018

(54) METHOD FOR THE PRODUCTION OF A DRILLING JIG

(76) Inventor: Marcus Abboud, Setauket, NY (US)

( * ) Notice: Subject to any disclaimer, the term of this patent is extended or adjusted under 35 U.S.C. 154(b) by 1653 days.

(21) Appl. No.: 13/203,244

(22) PCT Filed: Feb. 24, 2010

(86) PCT No.: PCT/EP2010/052333
§ 371 (c)(1),
(2), (4) Date: Nov. 3, 2011

(87) PCT Pub. No.: WO2010/097405
PCT Pub. Date: Sep. 2, 2010

(65) Prior Publication Data
US 2012/0053593 A1    Mar. 1, 2012

(30) Foreign Application Priority Data
Feb. 27, 2009   (DE) .................. 10 2009 010 699

(51) Int. Cl.
| | | |
|---|---|---|
| *A61B 17/56* | (2006.01) | |
| *A61C 1/08* | (2006.01) | |
| *A61B 17/17* | (2006.01) | |
| *A61C 13/00* | (2006.01) | |

(52) U.S. Cl.
CPC ............ *A61C 1/084* (2013.01); *A61B 17/176* (2013.01); *A61C 13/0004* (2013.01)

(58) Field of Classification Search
USPC ........... 606/96-98, 104; 433/72, 75, 76, 215
See application file for complete search history.

(56) References Cited

U.S. PATENT DOCUMENTS

| | | |
|---|---|---|
| 6,319,006 B1 | 11/2001 | Scherer et al. |
| 2009/0274990 A1 | 11/2009 | Kim |
| 2010/0028826 A1 | 2/2010 | Jacotti |
| 2010/0035201 A1 | 2/2010 | Beck et al. |

FOREIGN PATENT DOCUMENTS

| | | | |
|---|---|---|---|
| DE | 195 10 294 A1 | 10/1996 | |
| DE | 199 52 962 A1 | 5/2001 | |
| EP | 1 043 960 B1 | 10/2000 | |
| EP | 2 072 018 A1 | 6/2009 | |
| WO | WO 2008/038471 A1 | 4/2008 | |
| WO | WO 2008/117323 A1 | 10/2008 | |
| WO | WO 2008117323 A1 * | 10/2008 | |
| WO | WO 2010/018565 A1 | 2/2010 | |

* cited by examiner

*Primary Examiner* — Kevin T Truong
*Assistant Examiner* — Tracy Kamikawa
(74) *Attorney, Agent, or Firm* — Norman B. Thot

(57) ABSTRACT

A method for producing a drilling jig to drill a drill hole in a jaw of a patient to insert a tooth implant therein includes providing a prosthesis with an individualized part and a standardized plate part. The prosthesis is adapted to and placed on the at least one of the jaw and teeth of the patient. A three-dimensional digital jaw model is created. The tooth implant is designed and digitally constructed in the three-dimensional digital jaw model. A drilling model is formed with a drilling model drill channel using the three-dimensional digital jaw model showing the planned tooth implant. The drilling model is mounted on the prosthesis. A prosthesis drill channel is drilled into the prosthesis in alignment with the drilling model drill channel to form the drilling jig for drilling the drill hole in the jaw of the patient for the tooth implant.

2 Claims, 2 Drawing Sheets

METHOD FOR THE PRODUCTION OF A DRILLING JIG

CROSS REFERENCE TO PRIOR APPLICATIONS

This application is a U.S. National Phase application under 35 U.S.C. § 371 of International Application No. PCT/EP2010/052333, filed on Feb. 24, 2010 and which claims benefit to German Patent Application No. 10 2009 010 699.5, filed on Feb. 27, 2009. The International Application was published in German on Sep. 2, 2010 as WO 2010/097405 A1 under PCT Article 21(2).

FIELD

The present invention provides a method for the production of a drilling jig for drilling a drill hole in a patient's jaw for the purpose of inserting a tooth implant.

BACKGROUND

A dental prosthesis, e.g. a crown or a bridge, may be supported by an implant, hereinafter referred to as a tooth implant. Generally, such an implant is a rotationally symmetric implant and, in this respect, such an implant usually is a screw implant. Before the rotationally symmetric implant is placed into the patient's jaw, the patient's jaw is prepared by drilling a drill hole for the implant.

The spatial position of the implant drill hole in the patient's jaw and of the crown to be eventually fastened on the implant, are planned at a computer and with the help of a three-dimensional digital jaw model captured using imaging techniques, which model represents the patient's jaw and the existing teeth of the patient. After the implant drill hole in the jaw has been planned and defined spatially, the implant drill hole must be drilled in the patient's jaw in exactly the manner as planned.

For this purpose a drilling jig is used which is set on the patient's jaw or, as far as existing, on the patient's teeth in a defined spatial orientation and which has a drill channel for guiding a drill, which channel may also be referred to as a guiding channel. For the drilling jig to be placed in a defined spatial orientation with respect to the patient's jaw, it has to present a corresponding negative of the occlusal surfaces of the teeth or of the patient's jaw. The drilling jig's drill channel serves as an axial guide for the drill with which the drill hole is drilled into the patient's jaw, and may also serve as a depth stop, if so desired.

DE 199 52 962 A describes how the tooth implant and the corresponding implant bore are planned digitally from all of the digital three-dimensional information about the patient's jaw, the patient's teeth etc. A complex drilling jig is eventually produced therefrom, having the negative of the occlusal surfaces of the still existing teeth of the patient and a drilling jig drill channel. EP 1 043 960 describes producing a complete drilling jig from a single piece.

Producing such drilling jigs is technically challenging, in particular because of the complex shape of the negative of the occlusal surfaces of the neighboring teeth of the planned implant, so that an expensive CAD apparatus is required for this purpose and rather long manufacturing times occur in the production of a drilling jig.

An adjustable drilling device is described in DE 195 10 294 A with which a drill channel is drilled into a surgical jig so that eventually a drilling jig is obtained for drilling the drill hole necessary for the planned implant into the patient's jaw.

An aspect of the present invention is to provide a method for the production of a drilling jig and a drilling jig, which require little effort in the production of the finished drilling jig.

In an embodiment, the present invention provides a method for producing a drilling jig to drill a drill hole in a jaw of a patient to insert a tooth implant therein which includes providing a prosthesis with an individualized part and a standardized plate part. The prosthesis is adapted to and placed on the at least one of the jaw and teeth of the patient. A three-dimensional digital jaw model is created. The tooth implant is designed and digitally constructed in the three-dimensional digital jaw model. A drilling model is formed with a drilling model drill channel using the three-dimensional digital jaw model showing the planned tooth implant. The drilling model is mounted on the prosthesis. A prosthesis drill channel is drilled into the prosthesis in alignment with the drilling model drill channel to form the drilling jig for drilling the drill hole in the jaw of the patient for the tooth implant.

BRIEF DESCRIPTION OF THE DRAWINGS

The present invention is described in greater detail below on the basis of embodiments and of the drawings in which.

DETAILED DESCRIPTION

Figure 1:
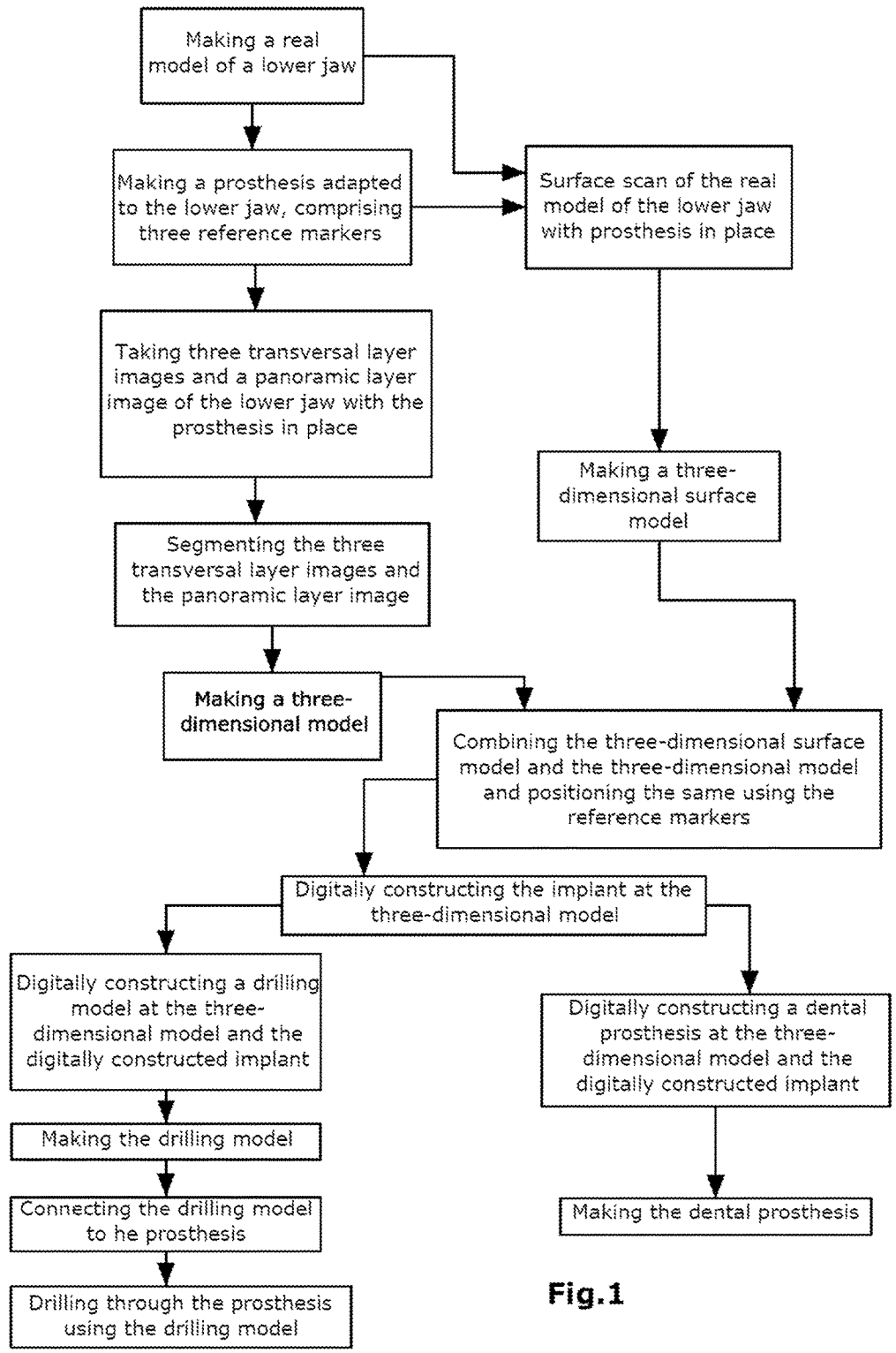
FIG. 1 illustrates the sequence of method steps.

In an embodiment of the present invention, a prosthesis is adapted to the jaw and/or the teeth of a patient. Hereinafter, this prosthesis is also referred to as a reference plate, since it serves as a spatial reference by establishing a defined fixed spatial reference to the patient's jaw or the patient's teeth while the three-dimensional digital jaw model is captured, while supporting the drilling model, and finally while serving as the drilling jig.

The reference plate (prosthesis) may be produced, for example, by taking a negative impression of the patient's jaw or the patient's teeth, using an impression compound. This negative impression is a part of the reference plate so that the reference plate (prosthesis) can always be set on the patient's jaw or the patient's teeth in an identical spatial position. The reference plate (prosthesis) further comprises at least one coupling part and at least two reference markers. The reference markers are opaque in all subsequent imaging processes, i.e., they are visible in particular during the subsequent capturing of a three-dimensional digital jaw model.

After the reference plate (prosthesis) has been set on the patient's jaw or the patient's teeth, known imaging methods and devices are used to make a three-dimensional digital jaw model of the jaw and the teeth of the patient as well as of the reference markers of the reference plate (prosthesis) set thereon.

When the jaw model has been captured, the tooth implant is digitally planned and constructed at a computer. The spatial orientation of the tooth implant in the patient's jaw is, for example, planned and defined, whereby the spatial orientation and the depth of the drill hole in the patient's jaw into which the implant is to beset or screwed on later, are also defined. By defining the spatial orientation of the drill hole in the patient's jaw, the spatial orientation of a drill channel in the drilling jig is defined as well.

A drilling model, which model will hereinafter also be referred to as a transfer jig, is thereafter digitally constructed using the digital three-dimensional jaw model and the digitally constructed implant including the planned and spatially defined drill hole in the jaw. This can, for example, occur in an automated manner. The transfer jig (drilling model) thus constructed is adapted to the reference plate (prosthesis) and to the coupling parts of the reference plate (prosthesis) such that the transfer jig (drilling model) can be fixed to the reference plate (prosthesis) in a defined orientation and position. The constructed transfer jig (drilling model) comprises a drilling model drill channel that is in exact axial alignment with the later reference plate/drilling jig drill channel and with the planned jaw drill hole for the implant when the transfer jig is fixed on the reference plate and the latter is fixed on the jaw.

Based on the digital jaw model including the planned tooth implant and the planned implant drill hole, the transfer jig (drilling model) is produced, with the transfer jig (drilling model) comprising a guiding drill channel and a coupling part that is adjusted to the coupling part of the reference plate (prosthesis) such that the transfer jig (drilling model) can be fixed to the reference plate (prosthesis) in a defined orientation and position.

The transfer jig (drilling model) is connected to the reference plate (prosthesis) such that coupling parts fix the transfer jig (drilling model) to the reference plate (prosthesis) in a defined orientation and position.

A drill guided in the transfer jig drill channel is then used to drill a reference plate drill channel into the reference plate (prosthesis), whereby the reference plate (prostheses) becomes a drilling jig.

A dentist places the drilling jig onto the patient's jaw or the patient's teeth in the position defined by the negative impression. During the subsequent drilling of the drill hole into the patient's jaw, the drill channel serves as a guide for the drill.

The method of the present invention makes it possible to produce a drilling jig in a simple manner. The fact that the transfer plate (prosthesis) eventually forms the drilling jig allows for an exact positioning of the drilling jig on the patient's jaw since the drilling jig is constructed directly and without any intermediate molds from the transfer plate (prosthesis).

In an embodiment, the transfer plate (prosthesis) used in the method of the present invention may, for example, comprise a standardized part including the coupling parts and the reference markers, and an individualized part that will be or is adapted to the body part, i.e., the patient's jaw and/or the patient's teeth. The transfer jig (drilling model) may also be a standardized part adapted to the standardized part of the reference plate (prosthesis). The drill channel can, for example, be drilled into the standardized transfer jig (drilling model) using a digitally controlled drill.

In practice, the standardized transfer jigs and reference plates may be used as follows:

First, the attending dentist takes a (negative) mechanical impression of the relevant jaw of a patient or of the associated teeth of a patient using a suitable impression compound. The dentist has a stock of standardized plate parts of reference plates. After the impression compound has cured, the negative impression body thus obtained is fixed, e.g. glued, on a reference plate by its planar rear side that is opposite the impression side. The impression body is an individualized part and is combined with the standardized plate part to form a reference plate.

The impression compound may alternatively applied onto the plate part of the reference plate before taking the impression, and the impression compound may be set on the patient's jaw together with the plate part to take the impression. For the curing of the impression compound, the impression compound can be removed from the jaw together with the plate part of the reference plate.

The impression can also be taken extra-orally using a so-called real model of the patient's jaw.

When the impression compound has been cured, the reference plate is again placed on the patient's jaw by the impression side. Two-dimensional or three-dimensional imaging methods are thereafter used to create a three-dimensional digital jaw model including the patient's jaw, the teeth and the reference markers of the reference plate.

At a computer the dentist thereafter plans and constructs the tooth implant in the three-dimensional jaw model. Here, the spatial orientation of the longitudinal axis of the implant in the patient's jaw is defined, and the spatial orientation and possibly the depth of the implant drill hole in the patient's jaw are defined. The entire data set, comprising the digital jaw model and the information about the spatial orientation of the implant drill hole, may now transmitted by the dentist to a central transfer jig production site via, for example, the internet.

Based on the jaw model data set transmitted, a drill channel is drilled into the standardized transfer jig at the transfer jig production site such that this drill channel would be in exact alignment with the planned implant drill hole if the transfer jig were fixed to the reference plate set on the patient's jaw. When the drill channel has been drilled, the transfer jig can be shipped to the dentist.

The dentist places the transfer jig onto the reference plate in a position defined and standardized by the coupling parts, inserts a drill into the transfer jig drill channel and drills a drill channel into the reference plate in alignment with the transfer jig drill channel. The transfer jig is then removed from the reference plate. The reference plate, now having a drill channel, has thus become a drilling jig that may be applied onto the patient's jaw.

After having been set on the patient's jaw, the drill channel of the drilling jig is used by the dentist as a guide bore for the drill with which the drill hole for the implant is drilled into the patient's jaw.

The reference plate (prosthesis) and/or the transfer jig (drilling model) may also comprise an articulation point for the articulated connection of a bite fork thereto.

It is also possible that the reference plate (prosthesis) and/or the transfer jig (drilling model) are connectable to an articulator.

In this manner, it is possible to check the information contained in the prosthesis and/or the drilling model by means of a simulation of the jaw joint movements or to use them in constructing a dental prosthesis.

In an embodiment, the method of the present invention can, for example, comprise the additional step:

digitally constructing a dental prosthesis based on the digital three-dimensional jaw model or the digitally constructed implant, wherein the dental prosthesis is adapted to the digital surface model.

The present invention thus advantageously allows the same digital models employed in constructing the implant to also be used in the construction of the dental prosthesis that is later fastened on the implant. This allows for an exact construction of the dental prosthesis. Adapting the dental prosthesis to the digital surface model makes it possible to adapt the dental prosthesis to the adjacent teeth, the so-called abutment teeth, in an advantageous manner.

In an embodiment, the dental prosthesis can, for example, be produced using a CAM method.

In an embodiment, the present invention further provides a drilling jig for preparing a bone for a medical implant or to drill a drill hole for a tooth implant, the drilling jig having a reference plate (prosthesis) adapted to at least one portion of the body part or to the patient's jaw, the transfer plate (prosthesis) comprising coupling parts for coupling model parts thereto, such as a drilling model, and a drilling model adapted to the medical implant and the prosthesis, the prosthesis and the drilling model being connectable via the coupling parts. In this context, the drilling jig is to be understood as a system formed by the prosthesis and the drilling model.

In combination with the method of the present invention, the present invention provides a drilling jig of low manufacturing cost which can advantageously be positioned exactly on a portion of a body part or on the jaw, respectively.

In an embodiment, the present invention provides that the reference plate (prosthesis) comprises at least two reference markers suited to form reference points in digital images of the reference plate (prosthesis). It is thus possible to allow for a digital construction of the drilling model using the above-described method.

The prosthesis can be of a bipartite design and comprises an individualized part adapted to the at least one portion of a body part or to the jaw and a standardized plate part.

This advantageously allows for an economic production of the prosthesis.

The present invention provides, for example, that the standardized plate part comprises the at least two reference markers and the coupling parts.

It may be provided that the drilling model and/or the prosthesis have an articulation point for articulating a bite fork thereto.

The prosthesis and/or the drilling model can, for example, be adapted for a connection with an articulator.

The information included in the prosthesis and/or the drilling model can thereby be checked during a simulation of the jaw joint movement or it may be used in constructing a dental prosthesis.

In an embodiment of the present invention, a method for planning a medical implant may comprise the following steps:

producing a prosthesis adapted to at least one portion of a body part, wherein the prosthesis comprises at least two reference markers;

creating at least one transversal layer image of the at least one portion of the body part, wherein, as the images are created, the prosthesis is situated on the body part, such that the at least two reference markers of the prosthesis are visible in at least one of the transversal layer images;

segmenting the at least one transversal layer image and forming a digital three-dimensional model of at least a part of the at least one portion of the body part from the at least one transversal layer image, the digital three-dimensional model including position data of the at least two reference markers;

capturing surface data of the at least one portion of the body part or of a real model of the at least one portion of the body part, wherein, during the capturing of the surface data, the prosthesis is situated on the body part or on the real model, and creating a digital three-dimensional surface model of the at least one portion of the body part using the surface data, the digital three-dimensional surface model including position data of the at least two reference markers;

combining the digital surface model and the digital three-dimensional model and positioning the digital three-dimensional model with respect to the digital surface model using the position data of the at least two reference markers; and digitally constructing the medical implant based on the digital three-dimensional model as well as on its position in the digital three-dimensional model, the digitally constructed implant and its position being adapted to the digital surface model.

The method is advantageous in that three-dimensional data of the inner parts must be available only for a part of the at least one portion of the body part, which data are obtained from two-dimensional layer images. Since the prosthesis is adapted to the at least one portion of the body part, the prosthesis can always be positioned at exactly the same position of the body part so that, when the layer images are taken and the surface data are captured, the prosthesis always has exactly the same position with respect to this body part.

This allows for an exact positioning of the three-dimensional model created from the layer images with respect to the digital three-dimensional surface model created from the surface data, using the reference markers which may be provided e.g. as spheres on the prosthesis.

It is ultimately not necessary for the capturing of the surface data to take a surface scan of the at least one portion of the body part, but it is also possible to scan an already existing real model of the at least one portion of the body part with the prosthesis in place. This may be advantageous, for example, when the method is used to plan dental implants, since often real models of a portion of a patient's body part, such as a portion of the jaw, are already available. The patient therefore does not have to undergo another capturing of data, because the surface data can be determined in the laboratory using the real model and the prosthesis. The real model may have been made in a conventional manner by means of an impression. It is also possible that the real model is based on medical data, such as data from a surface sensor obtained during a computer tomography or digital volume tomography (DVT).

Since the digital three-dimensional model also includes inner tissue parts of the at least one portion of the body part, an advantageous construction of a medical implant is possible since, for example, nerve tracts inside the body part or the like can be taken into consideration. At the same time, the positioning of the digital three-dimensional model with respect to the digital three-dimensional surface model makes it possible to adapt the digitally constructed implant to the surrounding. For example, if the method is used in a dental context, it is possible to adapt the implants to neighboring teeth since the position and the size of the neighboring teeth can be taken from the surface model.

It may be provided that a panoramic layer image or a longitudinal section image of the at least one portion of the body part is taken in addition to the transversal layer image, with the prosthesis being in place on the body part as the panoramic layer image or the longitudinal section image is taken, such that at least one of the at least two reference markers of the prosthesis is discernible on the panoramic layer image or the longitudinal section image and that, for the creation of the digital three-dimensional model, the panoramic layer image or the longitudinal section image is used in addition to the at least one transversal layer image.

Since X-ray apparatuses that allow taking transversal layer images mostly also allow taking panoramic layer images or longitudinal section images, such a panoramic layer image or longitudinal section image can be made with little effort and at low cost. Since the panoramic layer image or the longitudinal section image extends approximately orthogonally to at least one of the approximately parallel transversal layer images, the accuracy of the digital three-dimensional model can be improved by adding the panoramic layer image or the longitudinal section image. It may be provided that the panoramic layer image or the longitudinal section image is segmented when the digital three-dimensional model is formed.

In an embodiment of the present invention, the method may include another step relating to the production of a real model that represents at least a portion of a body part, wherein the prosthesis is, for example, made using this real model and/or the surface data are determined based on the real model. The production of the real model may, for example, be the first step of the method.

Due to the production of a real model, it is possible to produce the prosthesis and the capture the surface data in a simple manner in the laboratory so that no additional consultation is required from the patient. The real model can be produced using a conventional impression or data from a surface scan of the at least one portion of the body part. In addition or as an alternative, data from a computer tomography or a digital volume tomography may also be used.

FIG. 1 schematically illustrates the course of a method for planning a dental implant in the lower jaw of a patient.

First, a real model of the lower jaw 1 and of the teeth 5 of a patient is made in a conventional manner. This can be effected by a surface scan of the jaw 1 and the teeth 5 or with the use of data from computer tomography or digital volume tomography. It is also possible to create the real model in a conventional manner by taking a mechanical impression of the jaw 1.

A prosthesis 3 adapted to the lower jaw 1 is thereafter formed, comprising two or three reference markers 7. The prosthesis 3 may be adapted to the real model of the lower jaw 1 or directly to the lower jaw 1 of the patient. The prosthesis 3 may be adapted to the jaw 1 and/or the teeth 5 for example in a conventional manner by taking an impression using known impression compounds. The cured impression 3b of the jaw, which is an individualized part 3b of the prosthesis 3, may be connected, e.g. glued, to a standardized prosthesis plate part 3a to form the prosthesis 3.

A surface scan is performed on the real model of the lower jaw 1 with the prosthesis 3 in place, with the surface scan also capturing image data of the reference markers 7 of the prosthesis 3. It is alternatively possible to also make the surface scan on the lower jaw 1 of the patient, in which case the prosthesis 3 is in place on the lower jaw 1 of the patient.

A three-dimensional surface model is created from the surface scan of the lower jaw 1 with the prosthesis 3 in place, wherein the position data of the reference markers 7 of the prosthesis 3 are included in the surface model.

Three transversal layer images and a panoramic layer image or a longitudinal section image of the lower jaw 1 of a patient are then taken, with the prosthesis 3 being in place on the lower jaw 1 of the patient as the images are taken. The transversal layer images and the panoramic layer image or the longitudinal section image are taken of that portion of the lower jaw 1 of the patient in which the implant is later to be implanted on. Here, the longitudinal section image extends orthogonally to at least one of the transversal layer images and preferably centrally with respect to at least one of the transversal layer images.

The transversal layer image and the panoramic layer image or the longitudinal section image may be taken with a conventional dental X-ray apparatus.

The transversal layer images and the panoramic layer image or the longitudinal section image are then segmented by digitally marking the portions of the image that belong to a tissue part of the lower jaw or a tooth on the different images. The reference markers 7 of the prosthesis 3 also visible on the images are also segmented.

By segmenting the individual portions of the images a three-dimensional model of the captured portion of the lower jaw 1 can be digitally formed, the three-dimensional model including the position data of the reference markers 7 of the prosthesis 3 in place.

The digitally formed three-dimensional model may then be combined with the three-dimensional model obtained from the surface scan, it being possible to position the two models exactly with respect to each other due to the reference markers 7.

The combination of the two models forms a common jaw model that includes the portion of the lower jaw 1, where the implant is to be implanted, in a three-dimensional form with information about the inner tissue parts, whereas the other portions of the lower jaw only exist as surface data.

Based on this jaw model, the implant can now be constructed digitally in the three-dimensional model. Here, it is not only possible to take into consideration the inner tissue parts existing in the portion of the lower jaw 1 where the implant is to be implanted, but it is also possible to adapt the implant to the neighboring teeth 5 that can be seen in the three-dimensional surface model.

An appropriate implant can then be selected or produced based on the digital construction of the implant.

Using the digital jaw models formed, a drilling jig 10 is made that is used in drilling the drill hole 21 in the jaw 1 necessary for the implant. It may be provided that a drilling model 11 is digitally constructed based on the three-dimensional model and the digitally constructed implant.

The drilling model 11 can then be made, e.g. with the help of a 3D printer or with the use of a construction method. It is provided that the drilling model 11 is adapted to the prosthesis 3. It is thus possible that the drilling model 11 is a standardized part, the shape of the drilling model 11 obtained by digital construction being transferred in a conventional manner to the standardized part by means of a material removing method. The finished drilling model 11 has a drill channel 15 that forms a drill guide for drilling the drill channel 20 in the prosthesis 3.

The drilling model 11 is then connected to the prosthesis 3. For this purpose, the prosthesis 3 may comprise connecting parts and/or coupling parts 9, for example, to which the drilling model 11 or the drilling model coupling parts 13 are adapted.

The drilling model 11 is then used to drill the prosthesis drill channel 20 in the prosthesis 3 so that the prosthesis 3 can form the drilling jig 10 either by itself or in combination with the drilling model 11.

The use of the prosthesis 3 as a drilling jig 10 or as a part of the drilling jig 10 is advantageous because the prosthesis 3 is used to obtain the data necessary for the construction of the drilling jig 10 and the positioning of the drilling jig 10 for the drilling of the drill hole 21 is effected using the same prosthesis 3. This provides an exact positioning of the drilling jig 10 on the jaw 1 for the drilling of the drilling hole 21 in the jaw 1.

The method may further provide that a dental prosthesis can be digitally constructed using the three-dimensional model and the digitally constructed implant, with the dental prosthesis possibly being adapted to the three-dimensional surface model. It is thus possible to also construct the dental prosthesis using the same data that are used to construct the implant, wherein the dental prosthesis can advantageously be adapted to the digitally constructed implant and to the neighboring teeth that are visible in the three-dimensional surface model.

The dental prosthesis can then be produced in a further step, e.g. with the help of a CAM method, such as stereolithography, or 3D printing or a material removing method, e.g. a milling method.

Figure 2:
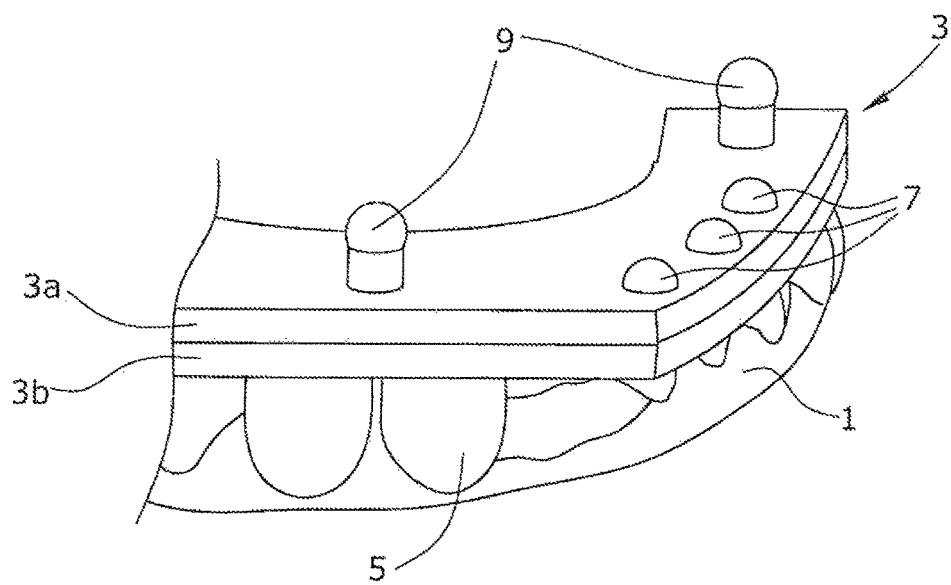
FIG. 2 is a schematic illustration of a lower jaw with the prosthesis of the present invention in place.

FIG. 2 is an exemplary schematic illustration of a lower jaw 1 of a patient with a prosthesis 3 set thereon.

Figure 3:
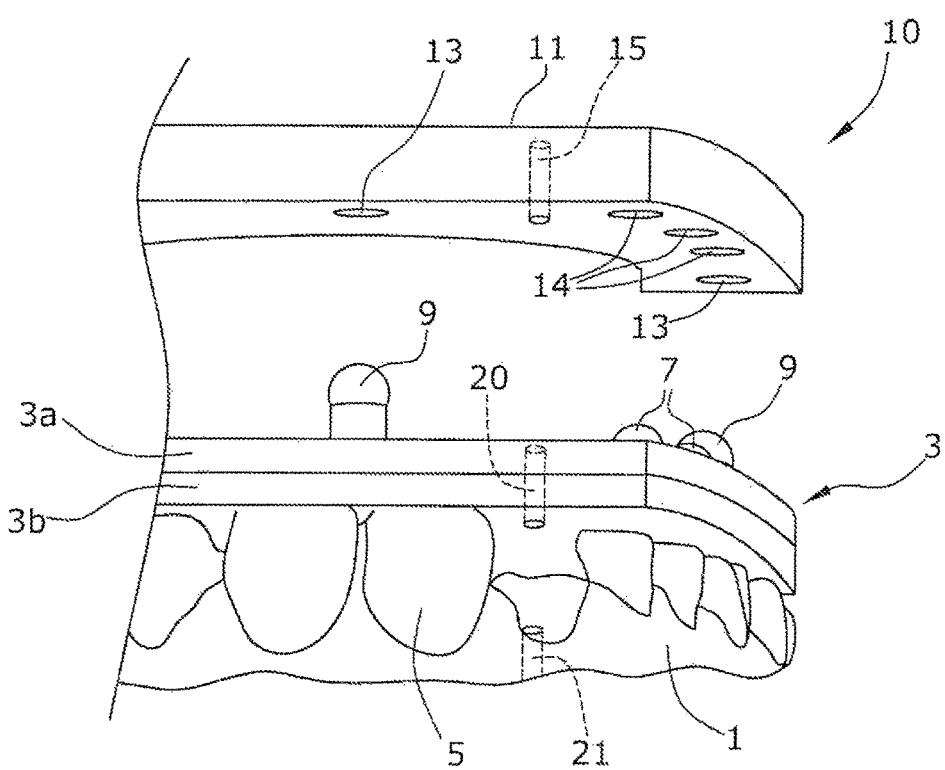
FIG. 3 is a schematic view of a lower jaw with the prosthesis in place and with a drilling model.

In the embodiment illustrated in FIGS. 2 and 3, the prosthesis 3 covers all teeth 5 still existing in the lower jaw of the patient. Of course, it is also possible that the prosthesis 3 is adapted to only a portion of the lower jaw 1 and covers only a portion of the lower jaw 1.

The prosthesis 3 has a lower side (front side) adapted to the teeth 5 of the lower jaw 1. On the upper side (rear side) of the prosthesis 3, two reference markers 7 are schematically illustrated. In the embodiment illustrated in FIGS. 2 and 3, the reference markers 7 are respectively formed as metal hemispheres. Of course, other shapes of the reference markers 7 are also conceivable, which are visible on layer images taken in the context of the above-described method and in the surface scan made according to the above-described method.

The prosthesis 3 further comprises a plurality of coupling parts 9 suited for coupling model parts thereto, for example for coupling the drilling model 11 thereto.

The prosthesis 3 may be of a unitary design. The prosthesis 3 can, for example, be of a multi-part design, with the prosthesis 3 comprising a standardized plate part 3a at or in which the reference markers 7 and the coupling parts 9 are arranged, and an individualized part 3b adapted to the jaw 1 of a patient, e.g. by taking an impression using known impression compounds.

FIG. 3 is a schematic illustration of a drilling jig 10 of the present invention. The drilling jig 10 is formed by the prosthesis 3 and a drilling model 11. The drilling model 11 is adapted to the prosthesis 3 and can be connected to the prosthesis 3. For this purpose, the drilling model 11 has coupling openings 13 in the lower side that are adapted to the coupling parts 9 of the prosthesis 3 and thus form the coupling parts 9, 13 of the drilling model. Further, the lower side of the drilling model 11 is provided with recesses 14 adapted to the reference markers 7. It is thus possible to connect the drilling model 11 flush with the prosthesis 3.

The drilling model 11 has a drill channel 15 constructed according to the method according to the present invention and transferred to the drilling model 11. Here, the drilling model 11 may be a standardized part onto which the drill channel 15 has been transferred using a material depositing or a material removing method, for example by drilling the drill channel 15. Using the above described method, the entire drilling model 11 may alternatively be formed as an individual part corresponding to the respective construction.

Using the drilling model 11 placed on the prosthesis 3 in a position defined by the coupling parts 9, 13, a drill channel 20 can be made or drilled in the prosthesis 3, which channel serves as a drill guide. The prosthesis 3 can form, either by itself or together with the drilling model 11, the drilling jig 10 for drilling a drill hole 21 in the lower jaw 1 into which the implant can then be inserted or screwed.

Since the above-described method uses the same prosthesis 3 for the construction of the implant, of the drill hole 21 for the implant in the jaw 1, and of the drilling jig 10, and the same prosthesis 3 is eventually also used in positioning the drilling jig 10, an exact preparation of the jaw 1 or drilling of the drill hole 21 for the implant in the jaw 1 is possible.

In a non-illustrated embodiment the prosthesis and/or the drilling model may comprise articulation points for a bite arc and/or an articulator so that the drilling model or the prosthesis can also be used in simulating the movement of the jaw joint. This makes it possible, for example, to check the prosthesis and/or the drilling model or to use the prosthesis and/or the drilling model in making or checking a dental prosthesis.

The present invention is not limited to embodiments described herein; reference should be had to the appended claims.

The invention claimed is:

1. A method for producing a drilling jig to drill a drill hole in a jaw of a patient to insert a tooth implant therein, the method comprising the steps of:
   providing a reference plate having a bipartite design, the reference plate comprising:
      an individualized part configured to be adaptable to at least one of the jaw and teeth of the patient, and
      a standardized plate part comprising at least two reference markers and at least one first coupling part;
   adapting the reference plate to the at least one of the jaw and teeth of the patient;
   placing the reference plate on the at least one of the jaw and teeth of the patient;
   creating a three-dimensional digital jaw model of the at least one of the jaw and teeth of the patient and the at least two reference markers;
   designing the tooth implant in the three-dimensional digital jaw model;
   digitally constructing the tooth implant in the three-dimensional digital jaw model;
   forming a drilling model with a drilling model drill channel using the three-dimensional digital jaw model showing the digitally constructed tooth implant, wherein the drilling model is a standardized part comprising at least one second coupling part configured to respectively couple with the at least one first coupling part;
   mounting the drilling model on the reference plate by coupling the at least one second coupling part with the respective at least one first coupling part; and
   drilling a reference plate drill channel into the reference plate in alignment with the drilling model drill channel, the reference plate with the reference plate drill channel thereby forming the drilling jig for drilling the drill hole in the jaw of the patient for the tooth implant,
   wherein the at least two reference markers are opaque when capturing a three-dimensional digital jaw model.

2. A method for producing a drilling jig to drill a drill hole in a jaw of a patient to insert a tooth implant therein, the method comprising the steps of:
   providing a reference plate having a bipartite design, the reference plate comprising:
      an individualized part configured to be adaptable to at least one of the jaw and teeth of the patient, and a standardized plate part comprising at least two reference markers and at least one first coupling part;
adapting the reference plate to the at least one of the jaw and teeth of the patient;
placing the reference plate on the at least one of the jaw and teeth of the patient;
creating a three-dimensional digital jaw model of the at least one of the jaw and teeth of the patient and the at least two reference markers;
designing the tooth implant in the three-dimensional digital jaw model;
digitally constructing the tooth implant in the three-dimensional digital jaw model;
forming a drilling model with a drilling model drill channel using the three-dimensional digital jaw model showing the digitally constructed tooth implant, wherein the drilling model is a standardized part comprising at least one second coupling part configured to respectively couple with the at least one first coupling part;
mounting the drilling model on the reference plate by coupling the at least one second coupling part with the respective at least one first coupling part; and
drilling a reference plate drill channel into the reference plate in alignment with the drilling model drill channel, the reference plate with the reference plate drill channel thereby forming the drilling jig for drilling the drill hole in the jaw of the patient for the tooth implant,
wherein the at least two reference markers are opaque when capturing a three-dimensional digital jaw model, and the reference plate is not opaque when capturing a three-dimensional digital jaw model.

* * * * *